United States Patent [19]
Loeb et al.

[11] Patent Number: 5,571,148
[45] Date of Patent: Nov. 5, 1996

[54] IMPLANTABLE MULTICHANNEL STIMULATOR

[76] Inventors: Gerald E. Loeb, 90 Bagot Street, Kingston, Ontario, Canada, K7L 3E5; Joseph H. Schulman, 10650 Comet Way, Santa Clarita, Calif. 91351

[21] Appl. No.: 288,289

[22] Filed: Aug. 10, 1994

[51] Int. Cl.⁶ .............................. A61N 1/36; H04R 25/00
[52] U.S. Cl. .................................. 607/57; 607/56; 607/55
[58] Field of Search .................................. 607/40–43, 46, 607/48, 49, 55–57, 62–65

[56] References Cited

U.S. PATENT DOCUMENTS

| | | | |
|---|---|---|---|
| Re. 31,031 | 9/1982 | Kissiah | 179/107 R |
| 3,751,605 | 8/1973 | Michelson | 179/107 R |
| 4,063,048 | 12/1977 | Kissiah | 179/107 R |
| 4,357,497 | 11/1982 | Hochmair et al. | 607/57 |
| 4,400,590 | 8/1983 | Michelson | 179/107 |
| 4,524,774 | 6/1985 | Hildebrandt | 128/421 |
| 4,611,598 | 9/1986 | Hortmann et al. | 607/57 |
| 4,721,551 | 1/1988 | Byers et al. | 204/47 |
| 4,819,647 | 4/1989 | Byers et al. | 128/642 |
| 4,991,582 | 2/1991 | Byers et al. | 128/419 |
| 5,193,539 | 3/1993 | Schulman et al. | 128/419 |
| 5,193,540 | 3/1993 | Schulman et al. | 128/419 R |
| 5,344,386 | 9/1994 | Schaldach | 607/48 |

OTHER PUBLICATIONS

Loeb, Gerald E., "The Functional Replacement of the Ear", 252:104–111 (1985).

White, Robert L., "System Design of a Cochlear Implant", *IEEE Engineering in Medicine and Biology Magazine*, Jun. 1987, pp. 42–46.

Hochmair et al, "An implanted audiotry eight channel stimulator for the deaf" Mar., 1981, Medical and Biological Engineering and Computing, pp. 141–148.

*Primary Examiner*—William E. Kamm
*Assistant Examiner*—Carl H. Layno
*Attorney, Agent, or Firm*—Fitch, Evan, Tabin & Flannery

[57] ABSTRACT

A multichannel stimulation system includes a plurality of implantable microminiature stimulators (microstimulators), each being connected to a respective implanted electrode or electrode array. Each microstimulator is selectively operable as controlled by an external (non-implanted) control unit. The electrode or electrode array is implanted so as to contact nerves and/or tissue that is to be stimulated. Operating power is inductively coupled from the control unit to the microstimulators. An information signal is also coupled to the microstimulators to control which of the microstimulators is to be activated to provide a stimulation pulse to its respective electrode. In one embodiment, the invention provides a cochlear prosthesis with an intracochlear electrode array being implanted within the human cochlea, and with selected electrodes of the array being connected to individual ones of the plurality of microstimulators. The control unit of such cochlear prosthesis includes a small external transmitter coil that is worn next to the skin where the microstimulators are implanted. The control unit generates a power signal and an information signal for powering and controlling the cochlear prosthesis.

48 Claims, 11 Drawing Sheets

(DIMENSIONS ARE TYPICAL FOR A COCHLEAR IMPLANT)

(DIMENSIONS ARE TYPICAL FOR A COCHLEAR IMPLANT)

(DIMENSIONS ARE TYPICAL FOR A COCHLEAR IMPLANT)

IMPLANTABLE MULTICHANNEL STIMULATOR

BACKGROUND OF THE INVENTION

The present invention relates to implantable stimulators, and more particularly to an implantable multichannel stimulator fashioned from a plurality of microstimulators connected in parallel, each microstimulator comprising a tiny self-contained stimulating device that is individually controllable from an external (non-implanted) power source, with each microstimulator providing its own stimulation output signal through a respective output electrode. One aspect of the invention relates to using such an implantable multichannel stimulator as an implantable cochlear prosthesis for electrically stimulating the auditory nerve of a profoundly deaf person.

Neurological disorders are often caused by neural impulses failing to reach their natural destination in otherwise functional body systems. Local nerves and muscles may function, but for various reasons, such as injury, stroke, or other cause, the stimulating nerve signals do not reach their natural destination. For example, paraplegics and quadraplegics have intact nerves and muscles and only lack the brain-to-nerve link, which stimulates the muscles into action.

While an implantable device that provides the missing brain-to-nerve link is not currently available, there are numerous stimulation devices available that provide electrical stimulation to excite muscle, nerve or other cells. Such devices have ranged in size and complexity from large, bulky systems feeding electrical pulses by conductors extending through the skin, to implanted stimulators which are controlled through modulated radio frequency (rf) signals, as set forth, e.g., in U.S. Pat. No. 4,524,774 (Hildebrandt), where modulated rf signals in the range of 27.12 MHz and 40.7 Mhz are used to control the implanted stimulator device. Through the selective positioning and control of such devices, it is thus possible to fashion a sequence of electrical stimulation signals that can control muscle, nerve or other cells in a desired manner, e.g., to excite arm muscles to move the arm, leg muscles to move the leg, and the like.

One area where externally-generated electrical stimulation pulses can be used to significant advantage is in the cochlea. The cochlea is part of the inner ear and resembles a snail shell within the temporal bone of the skull. It is conical in form and completes about 2¾ turns. It is about 5 millimeters (mm) in height and 9 mm in breath at its base. The cochlea, in cross section, has three main channels, an upper scala, a middle scala and a lower scala. These three channels are referred to respectively as the vestibular canal, the cochlear canal and the tympanic canal.

A membrane known as the basilar membrane separates the middle scala from the lower scala. Fibers of the auditory nerve (often referred to in the literature as the cochlear nerve) originate in the nerve cell bodies located in the spiral ganglion, which is located in the temporal bone, extending along and just medial to the three channels. Normally, these nerve cells contact hair cells that are located on the basilar membrane. Each hair cell terminates in about 20 cilia, or hair-like processes. Another membrane, known as the tectorial membrane, covers the cilia and causes a shearing action on the cilia when it moves with respect to the basilar membrane. Incoming sound waves into the middle scala cause the cilia to move or shear relative to the hair cells. Such movement or shearing action causes the hair cells to induce electrical pulses in the auditory nerve neurons going to the brain. The brain interprets such electrical pulses in the auditory nerve neurons as sound.

Unfortunately, the hair cells of the profoundly deaf are unable to generate electrical signals. Thus, no matter how much an incoming sound wave may be amplified, e.g., through the use of a conventional hearing aid device, the profoundly deaf are still unable to hear. It is thus apparent that there is a need in the art for a device that generates the electrical signals that would otherwise be generated by the hair cells of the profoundly deaf, thereby allowing such persons to experience the sensation of hearing.

Devices are known in the art that provide the sensation of hearing for the profoundly deaf by electrically stimulating the auditory nerve cells within the cochlea. Representative descriptions of such systems are presented below. However, all such known auditory-nerve stimulation systems suffer from one or more drawbacks, typically being much too large, too complex, too expensive, and/or ineffective to be of beneficial use to most persons who are profoundly deaf. What is needed, therefore, is a simple, inexpensive, easy-to-implant auditory-nerve stimulation system that can help larger numbers of the profoundly deaf to experience the sensation of hearing.

By way of example, a method of inducing hearing is taught in U.S. Pat. No. 3,751,605 (Michelson), wherein there is described a surgical procedure for implanting two opposing electrodes (conductors) within the lower scala of the cochlea. Incoming sound (pressure) waves are received and converted to electrical signals and amplified using electrical circuitry external to the ear. The amplified signals are then modulated and coupled to a receiver circuit implanted inside the ear, where the received signal is demodulated and applied to the two opposing electrodes. Such method, while representing a significant advance in the art at the time it was made, does not provide selective stimulation of the auditory nerve neuronal endings. That is, the system shown in the '605 patent is effectively a single channel system wherein all of the neuronal endings in contact with the electrode pair are effectively stimulated with the same signal.

Further, by way of example, U.S. Pat. No. 4,063,048 (Kissiah), which has been reissued as Reissue 31,031, teaches the use of a series of external, filter networks and generation of pulse signals of the same frequency as the audio signals. Such pulse signals are then applied by a plurality of electrodes to the portion of the cochlear nerve which normally transmits like signals in the normal hearing process. Thus, multiple channels are provided so that different portions of the cochlear nerve may be stimulated as a function of the frequency of the incoming signals. However, only the electrodes are implanted, which electrodes are connected to the female portion of a through-the-skin pin connector for making external connections with the external processing circuitry. Such pin connector, at best, may be source of irritation to the patient, and at worst, could easily be the source of infection. What is thus needed, is a simple, inexpensive multichannel stimulating system that does not require through-the-skin connections.

An additional example of a cochlear stimulator device is shown in U.S. Pat. No. 4,400,590 (Michelson). In the '590 patent, the cochlea is stimulated using a plurality of implanted electrodes driven by electronic circuitry and connected to the electrodes by way of a through-the-skin connector. The stimulating locations within the cochlea are selected as a function of the frequency of the electrical analog of the audio signal. One embodiment sums all frequencies and energizes all electrodes with the sum. Magnitudes are adjusted according to the particular user's requirements. However, only the multichannel electrodes are implanted in the cochlea, with a through-the-skin connection being made between the electrodes and the remaining electrical circuitry. While the '590 patent does mention that inductive and/or rf coupling could be used as a possible alternative to a through-the-skin connector, it does not teach how such coupling could be made, particularly in view of the fact that multiple channels are involved and any implanted circuitry would have to be extremely small, light weight, and consume very little power. What is thus needed is an auditory nerve stimulating system that avoids the use of through-the-skin connectors, while still providing multichannel operation.

Yet another example of a cochlear stimulator device is described in U.S. patent application Ser. No. 08/023,584, filed Feb. 26, 1993, incorporated herein by reference. The '584 application is a continuation of application Ser. No. 07/752,069, filed Aug. 29, 1993; which is a continuation in part of application Ser. No. 07/411,563, filed Sep. 22, 1989; all of which are assigned to the same assignee as the present application. Such application(s) describe a cochlear implant system known as the CLARION cochlear implant system, available from MiniMed Technologies, of Sylmar Calif. Such system includes an implantable cochlear stimulator (ICS) that drives a 16-contact intracochlear electrode, a wearable processor (WP), and a clinician's programmer (CP). The CLARION stimulator, or ICS, while representing a significant advance in the art, is nonetheless a relatively expensive unit due to the manner in which it must be manufactured. Moreover, should there be a component failure, it is possible that the entire ICS could malfunction depending upon the location and function of the failed component. What is thus needed is an implantable stimulator that is less expensive to manufacture and less susceptible to malfunctioning in the event of individual component failure.

The present invention addresses the above and other needs by providing a simple, reliable, inexpensive, easy-to-implant multichannel stimulation system, which system is particularly suited for stimulating the auditory nerve within the cochlea.

SUMMARY OF THE INVENTION

In accordance with one aspect of the present invention, there is provided a multichannel stimulation system made up of a plurality of implantable microminiature stimulators (hereafter "microstimulators"), each being connected to a respective implanted electrode pair or electrode array, and each being selectively operable as controlled by an external (non-implanted) control unit. The electrode pairs or electrode array are implanted so as to contact the nerves and/or tissue that is to be stimulated. Advantageously, the implantable microstimulators receive their operating power from the control unit, e.g., inductively, and thus there is no need to implant batteries (which have a limited operating life), or to use a through-the-skin connector, in order to provide power to and operate the implantable microstimulators. Further, the control unit transmits control signals to each microstimulator. One technique for transmitting such control signals is to modulate the power signal coupled to the microstimulators with the control signal, which control signal (when recovered through demodulation within each microstimulator) selectively controls the operation of each microstimulator. Hence, the control unit, without the need for any through-the-skin connectors, and without the need for any complex implanted multiplexing schemes or circuitry, is able to selectively control each implanted stimulator. Hence, the invention allows a desired stimulation pattern or sequence to be selectively provided through the plurality of electrodes.

Note, as used herein, the term "multichannel" refers to the ability to provide independent stimulation signals through separate electrodes, where each separate electrode (or electrode pair, or selected group of electrodes) represents the delivery point of a separate stimulation channel. In contrast, a single channel system always provides its stimulation signals through the same electrode(s), thus having only a single delivery point through which stimulation therapy may be provided.

Advantageously, each of the microstimulators included within the implanted stimulator of the present invention is totally isolated from and operates independently of the other microstimulators. Hence, should there be a failure of one of the microstimulators, such failure will not affect the operation of the other microstimulators, thus providing a degree of reliability not heretofore available in implantable multichannel stimulator devices.

In accordance with another aspect of the invention, the control unit is divided into two modules: (1) a transmitter coil module that is placed next to the skin near the location where the plurality of microstimulators are implanted, and (2) a control/power module that contains the power source (e.g., a rechargeable or replaceable battery) and the transmitter and modulation circuitry. In such modular embodiment, the control/power module is coupled to the transmitter coil module by a small unobtrusive cable.

In accordance with a further aspect of the invention, the electrode pairs or electrode array comprise an intracochlear electrode array designed for implantation within the cochlea, with selected electrodes of the array being connected to individual ones of the plurality of microstimulators. The microstimulators and intracochlear electrode array, except for some small electrode contacts which are interspersed along the length of the electrode array, are sealed in silicone rubber, or other elastomer material that is compatible with body tissue or fluids, as a solitary unit. Bipolar or unipolar stimulation may be utilized, depending upon how the individual electrode contacts are connected in circuit relationship with the microstimulators. Before implantation, the electrode array appears, as it were, to be a "pigtail" of such solitary unit, extending out from a body portion wherein the microstimulators are sealed. When implanted, the electrode array is inserted in the patient's cochlea, and the body portion is implanted in a tissue pocket formed underneath the skin behind the patient's ear. In operation, the patient wears a small external transmitter coil behind the ear, which transmitter coil is coupled to the control/power module. The control/power module provides operating power to the microstimulators and selectively controls each microstimulator as a function of the frequency of detected sound, sensed by a small microphone that forms part of the control/power module. Hence, the unit provides multichannel stimulation within the cochlea, thereby providing the patient with the sensation of hearing.

Advantageously, the microstimulators used by the present invention are extremely small devices that may be easily and inexpensively manufactured in large quantities. The microstimulators are identical to each other except for an address code that is built-in to (programmed into) each device. For a typical multichannel stimulation system, e.g., used to stimulate the cochlea, four to sixteen channels will usually be sufficient. Each channel typically requires its own, individually addressable microstimulator. Thus, during manufacture of the microstimulators, all of the microstimulators may be manufactured using the same process, except for one manufacturing step, where each microstimulator would be encoded or tagged with one of four to sixteen address codes. Then, in the final assembly of the multichannel stimulator, selected ones, e.g., one of each, of the separately addressable microstimulators are connected to an intracochlear electrode array, either in a bipolar or unipolar configuration, which array is a common part for each stimulator being made. Such commonality of components greatly facilitates the manufacture of the multichannel stimulator and significantly reduces its cost. As a result, large quantities of the multichannel stimulators can be manufactured at modest cost. When used as a cochlear prothesis, such large quantities thereby make it possible for larger numbers of the profoundly deaf to experience the sensation of hearing.

In accordance with another aspect of the invention, the multichannel microstimulators may include limited back-telemetry capabilities, allowing certain information related to the operation of the microstimulator, such as electrode impedance, or the strength of the transmission received from the control unit, or related to the environment wherein the microstimulator are implanted, to be sent back to the external control/power module. Such back-telemetered information may serve as a feedback signal to help optimally control the microstimulator(s), and/or as a diagnostic signal to assist in evaluating the performance and effectiveness of the microstimulator(s), such as to determine if the electrodes are positioned correctly and are intact.

It is thus a feature of the present invention to provide an implantable multichannel stimulator that is easy and inexpensive to manufacture.

It is another feature of the invention to provide a multichannel stimulator system having an implanted portion and a non-implanted portion, and wherein a main part of the implanted portion is very small, e.g., less than about 20 mm by 15 mm by 3 mm, and wherein such main part has a plurality of substantially identical microstimulator devices sealed therein.

It is yet an additional feature of the invention to provide a multichannel stimulator having, e.g., sixteen separate channels enclosed within a housing having thin walls made from a material that is transparent to radio frequency signals, e.g., glass or ceramic, yet wherein such walls are not so fragile that they cannot be readily implanted and remain implanted without breakage.

It is a further feature of the invention to provide such a multichannel stimulator unit that is hermetically sealed in a flexible enclosure suitable for implantation, thereby allowing the unit to form fit the skull or other bone structure at the implant location.

It is still another feature of the invention to provide an implantable multichannel stimulator that is made up of a plurality of common components, connected to a suitable electrode array.

It is an additional feature of the invention to provide such an implantable multichannel stimulator wherein the plurality of common components used therein each comprise a microstimulator that operates functionally independent of the other microstimulators. As a result, should one microstimulator fail, the others will not be adversely affected, and the operation of the multichannel stimulator can continue.

It is a further feature of the invention to provide such an implantable multichannel stimulator that does not require the use of through-the-skin connectors to couple control signals or power signals to the implanted portions of the stimulator.

It is yet another feature of the invention to provide such an implantable multichannel stimulator wherein the use of complex, power-consuming, implanted multiplexing circuitry is avoided.

It is an additional feature of the invention to provide a multichannel stimulator that, when coupled to an intracochlear electrode array, provides a way for the profoundly deaf to experience the sensation of hearing without requiring the use of through-the-skin electrical connectors to electrically contact the electrode array.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
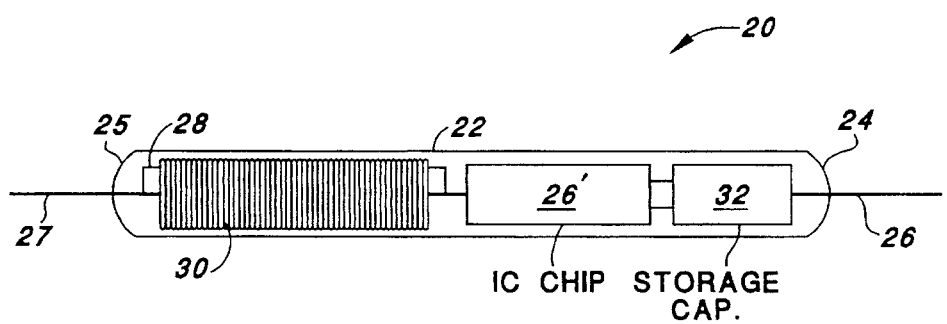
FIG. 1 depicts a microstimulator of the type that is used with the present invention.

Referring first to FIG. 1, there is shown a microstimulator 20 of the type that is used with the present invention. The microstimulator 20 is typically only about 10 to 15 mm in length, and comprises a quartz, glass, or ceramic tube or capsule 22, sealed at each end with a hermetic seal 24, 25. A first electrode 26 protrudes out from one end of the glass capsule 22, and a second electrode 27 protrudes out from the other end of the capsule 22. Such electrodes 26 and 27 are made from any suitable conductor, e.g., 0.025 to 0.150 mm diameter platinum-iridium wire.

Inside of the glass capsule 22 is the electronic circuitry associated with the microstimulator 20. In particular, in accordance with a preferred embodiment, the microstimulator 20 includes an integrated circuit (IC) chip 26', a ferrite core 28, a coil 30 wound around the ferrite core 28, and a storage capacitor 32. The IC chip 26', as explained more fully below, includes several logic and other circuits, including memory circuits.

All of the components and circuits within the microstimulator 20 are interconnected in circuit relationship so as to function as follows: (a) the coil 30 is inductively coupled to a modulated power signal that is generated external to the glass capsule 22; (b) the inductive coupling induces a modulated power signal in the coil 30; (c) the induced modulated power signal is rectified to provide operating power for the IC chip 26'; (d) power from the rectified power signal charges the storage capacitor 32; (e) the power signal is demodulated to extract an address word therefrom; (f) the extracted address word is compared to a preprogrammed microstimulator code stored in the microstimulator; and (g) if the extracted address code matches the preprogrammed microstimulator code, as determined by logic circuits included within the IC chip 26', the capacitor 32 is discharged through the two electrodes 26 and 27 with an amplitude and pulse width determined by the incoming data stream. In this manner, then, the operation of the microstimulator, i.e., the selective discharging of the storage capacitor 32, is controlled through appropriate modulation of the power signal.

Details associated with the design and construction of a representative microstimulator 20 that may be used with the present invention may be found in U.S. Pat. Nos. 5,193,539 and 5,193,540, incorporated herein by reference.

Figure 2A:
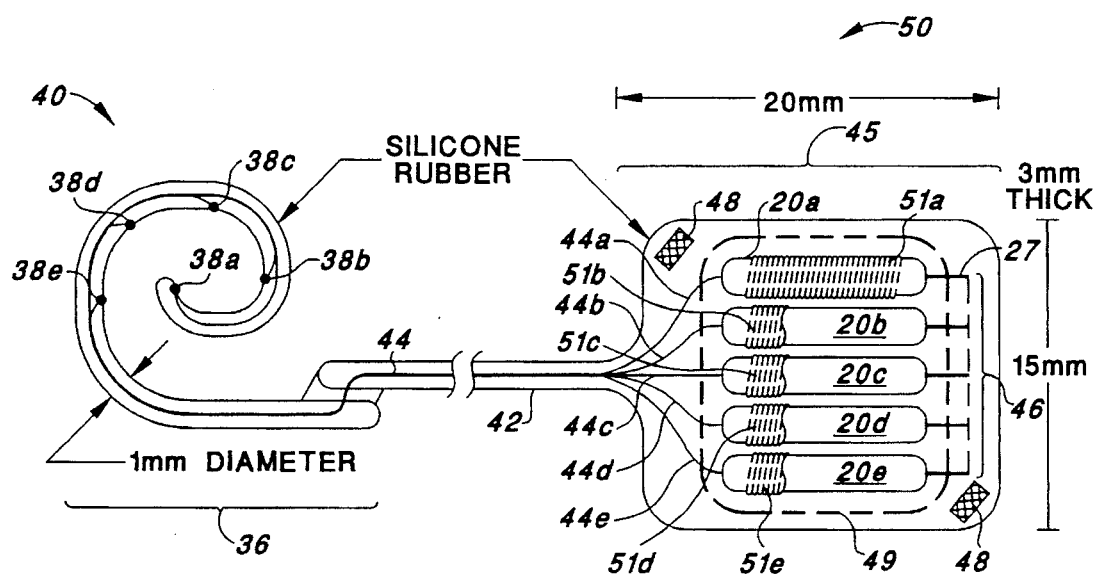
FIG. 2A illustrates how a plurality of microstimulators are mechanically held together in a silicon elastomer while being electrically connected to a cochlear electrode, thereby forming a multichannel stimulator in accordance with the present invention.

The present invention provides an implantable multichannel stimulator made up of a plurality of microstimulators 20, each connected to an electrode array 36, as shown in FIG. 2A. While the electrode array 36 shown in FIG. 2A is a cochlear electrode array, designed for implantation within the cochlea of a human ear, it is to be understood that such an electrode array is only exemplary of one of many possible types of implantable electrode arrays that may be used with the invention.

As shown in FIG. 2A, the electrode array 36 includes a plurality of stimulating electrode contacts, 38a, 38b, 38c, . . . 38n, each being spaced apart and electrically insulated from the others, and each being located more or less near a distal end 40 of a flexible body 42 that connects the array 36 with the microstimulators 20. Each electrode contact 38a, 38b, . . . 38n is in electrical contact with one or more of the electrodes 26 or 27 that protrude out from the ends of each microstimulator 20 through respective conductive wires 44a, 44b, 44c, . . . 44n.

For the configuration shown in FIG. 2A, which represents a unipolar stimulation configuration, five microstimulators 20a, 20b, 20c, 20d and 20e, are mechanically held together in a stimulator array 45, with the first electrode 26 (protruding from a first end of each microstimulator) being connected to a respective conductive wire 44a, 44b, 44c, 44d or 44e of the electrode array 36; and with the second electrode 27 (protruding from a second end of each microstimulator) forming an indifferent electrode 46. (It is noted that the electrodes 27 of each microstimulator may be electrically connected together, as suggested by the dotted line, to form a common indifferent electrode 46. Typically, however, each of the electrodes 27 will remain isolated from each other, thereby forming a plurality of separate indifferent electrodes 46.) In a preferred embodiment the dimensions of the microstimulator array 45 are on the order of 20 mm by 15 mm by 3 mm, thereby providing a sufficiently small device that can be readily implanted under the skin behind the ear or elsewhere. Stimulation for such configuration thus occurs between a selected one of the electrode contacts 38a, 38b, 38c, 38d or 38e, as determined by whichever microstimulator 20a, 20b, 20c, 20d or 20e is triggered by the address code included in the modulated power signal, and the indifferent electrode(s) 46. Such stimulation is a unipolar stimulation, with stimulation occurring between a given electrode and a common (indifferent) electrode.

Figure 5:
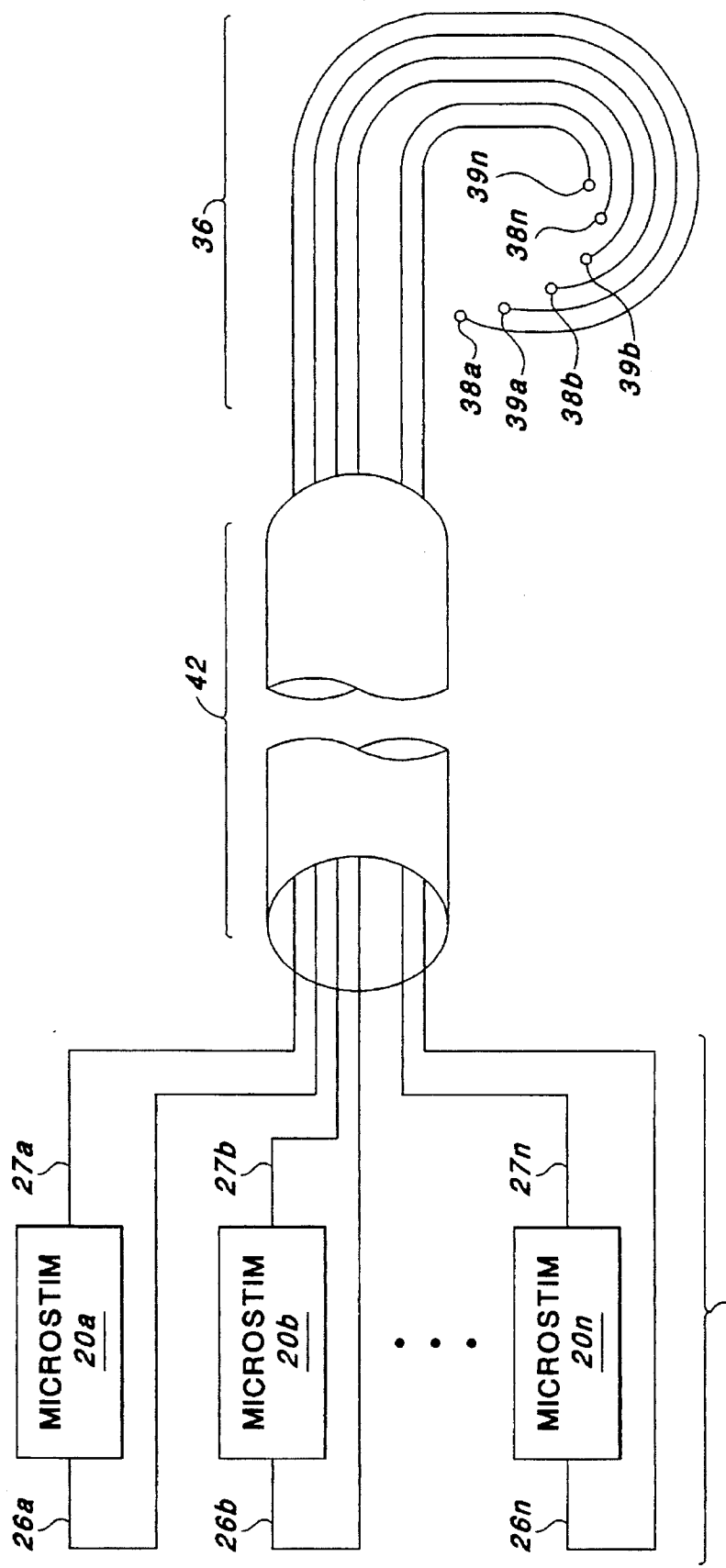
FIG. 5 illustrates how a multichannel stimulator made in accordance with the present invention may be used for bipolar stimulation.

It should be emphasized, however, that other stimulating configurations are possible with the present invention, and are included in the scope of the present invention, in addition to unipolar stimulation. For example, as shown in FIG. 5, bipolar stimulation may be achieved by coupling each of the protruding electrodes of each microstimulator 20a, 20b, . . . 20n (which electrodes are referenced as elements 26 and 27 with a letter appended thereto to designate the particular microstimulator to which the electrodes are attached, i.e., electrodes 26a and 27a originate with microstimulator 20a) to respective electrode contacts 38 and 39 located in the electrode array 36. Bipolar stimulation would thus occur between whichever electrodes, e.g., 38b and 39b, that are connected to the respective electrodes, e.g., 26b and 27b, of the microstimulator that is addressed or triggered, e.g., microstimulator 20b.

In a similar fashion, multipolar stimulation could occur by selective connection of a multiplicity of the electrode contacts to a corresponding multiplicity of the electrodes of the microstimulators. Indeed, there is no limit to the types of stimulation configurations and combinations that may be usable with the present invention. For example, a combination of bipolar and unipolar stimulators may prove to be optimum for a particular patient or application.

As shown in FIG. 2A, the electrode array 36 and the microstimulator array 45 are sealed or molded in a body compatible material, e.g., a plastic or elastomeric material. If flexibility is desired, such material may be, e.g., silicone rubber. If rigidity is desired, such material may be, e.g., epoxy. Regardless of the material used, the result is to form an integral implantable multichannel stimulator unit 50. Where the electrode array 36 is a cochlear electrode, as depicted in FIG. 2A, the distal end of the array 36 is coiled so as to fit within the cochlea, and the electrode contacts 38*a*, 38*b*, 38*n* are spaced so as to lie in close proximity to the spiral ganglion cells that form the cochlear nerve once the electrode array 36 is inserted into the cochlea. The conductive wires 44*a*, 44*b*, 44*c* . . . 44*n* form a cable that is also encapsulated within the silicone rubber, which silicone rubber (or other similar material) adds physical strength to the wires and prevents the electrode array 36 from breaking or disconnecting itself from the microstimulator array 45. The entire unit is thus implantable within a patient, with the electrode array 36 being implanted in the cochlea, and with the microstimulator array 36 being implantable under the skin or within a fleshy pocket behind the ear.

Included as part of the multichannel stimulator 50 is some sort of alignment means, such as a magnet or marker 48, that helps align the implanted microstimulator array 45, and more particularly the coils 30 (see FIGS. 1 and 4B) of the implanted microstimulator arrays, with an external coil (not shown in FIG. 2A, but shown in FIG. 4). The external coil is then connected to an external source that generates the modulated power signal. Optimum inductive coupling occurs between the internal coils 30 and the external coil when good alignment is achieved. Hence, maintaining proper alignment allows the modulated power signal to be a relatively low power signal.

To improve the coupling efficiency, and thereby allow the distance between the source of external power and each of the microstimulators 20 within the microstimulator array 45 to be increased while using less power, one embodiment of the present invention includes a focusing coil 49, incorporated around the perimeter of the array 45, to best capture the magnetic flux associated with an inductive coupling link. Such focusing coil 49 is coupled to individual coupling coils 51*a*, 51*b*, . . . 51*e*, each being wound, e.g., on the glass tube 22, around the respective coils of the microstimulators so as to best couple power and information to the respective microstimulators 20*a*, 20*b*, . . . 20*e*. The use of such focusing coil 49 with individual coupling coils 51 is explained more fully below in conjunction with FIGS. 4B–4D.

It is to be emphasized that while inductive coupling (a coupling of magnetic flux) is shown and described herein as the preferred technique for coupling power and information between the implantable microstimulator array 45 and an external source, such coupling is only exemplary and is only one of several available coupling techniques that may be used. Other types of coupling that may be used include optical coupling, rf (high frequency electromagnetic) coupling, acoustic coupling, infra red coupling, and the like. Any of such coupling techniques, or other power and informational coupling techniques, may be used with the present invention.

The design and construction of a cochlear array suitable for use with the present invention is shown in U.S. Pat. No. 4,819,647, incorporated herein by reference. In addition, other patents that teach various manufacturing techniques that may be useful in practicing various aspects of the present invention include U.S. Pat. No. 4,721,551, describing a technique for treating electrodes with iridium; and U.S. Pat. No. 4,991,582, describing a hermetically sealed ceramic and metal package for implantable electronic devices. Both the '551 and '582 patents are also incorporated herein by reference.

Figure 2B:
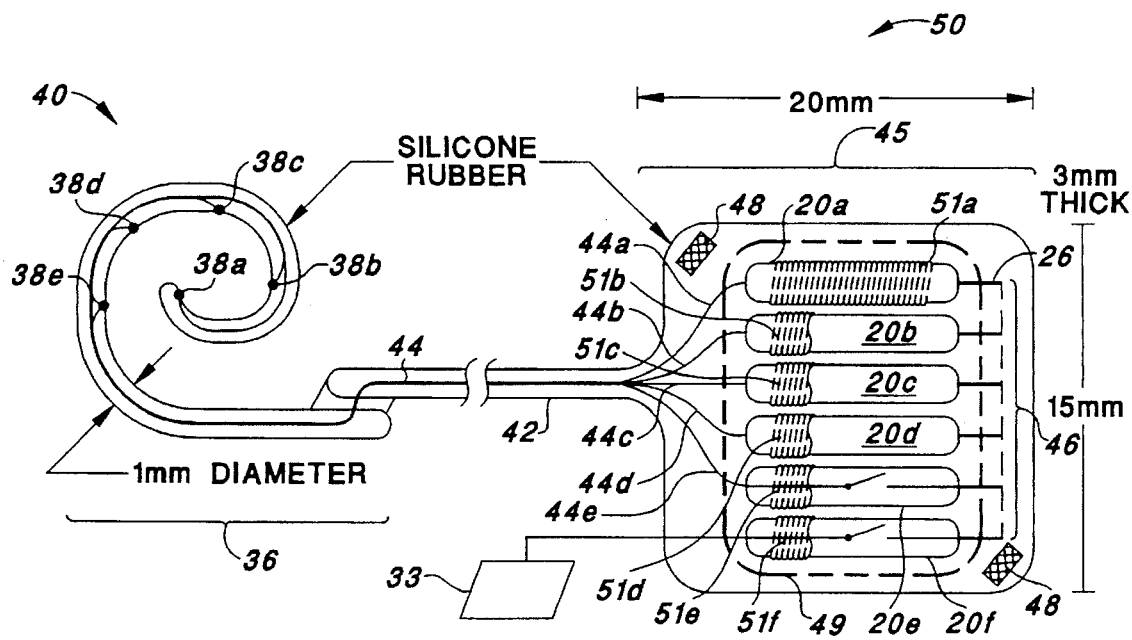
FIG. 2B depicts a multichannel stimulator as in FIG. 2A, and further illustrates the use of one of the microstimulators used as a simple switch to selectively configure the multichannel stimulator as either a unipolar or bipolar stimulator.

Referring next to FIG. 2B, there is shown an example of how the present invention may be used sequentially as either a bipolar stimulator or a unipolar stimulator. In such configuration, one of the microstimulators, e.g., 20*f*, within the array 45 is used as a simple switch to selectively connect or not connect the common electrode 46 to an indifferent electrode 33. The indifferent electrode 33 may be positioned at any convenient site to provide unipolar stimulation between the respective electrode contacts 38*a*, 38*b*, . . . of the electrode array 36 and the indifferent electrode 33. Another of the microstimulators, e.g., 20*e*, within the array 45 may likewise be used as a simple switch to selectively connect or not connect the common electrode 46 to a conductor 44*e* of the array 36 connected to an electrode contact 38*e*, thereby providing bipolar stimulation between the contact 38*e* and whichever other electrode contact 38*a*, 38*b*, . . . is activated through its respective microstimulator 20*a*, 20*b*, . . . .

Figure 3:
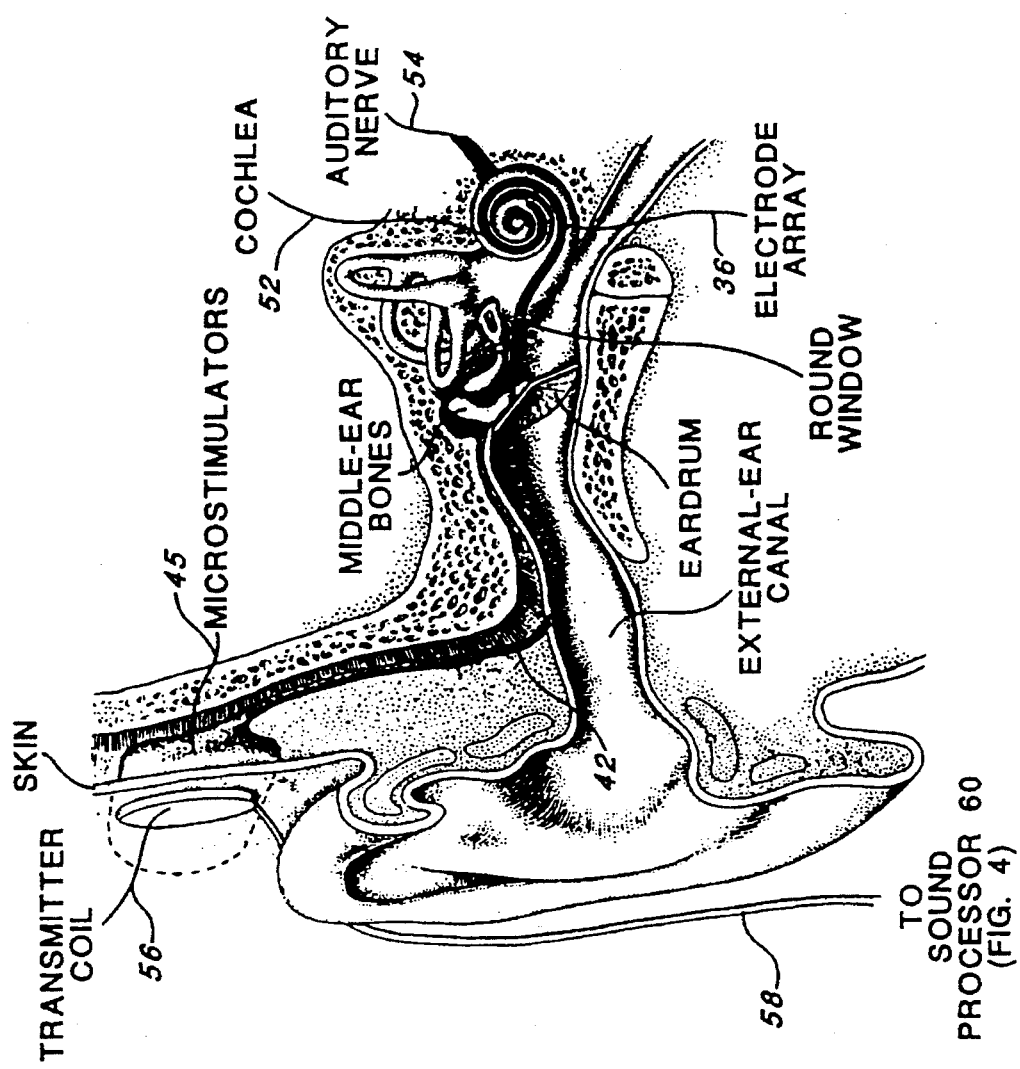
FIG. 3 illustrates the relative size of a multichannel stimulator used as a cochlear prothesis compared to a human ear, and illustrates how such stimulator is implanted within the cochlea.
Figure 3:
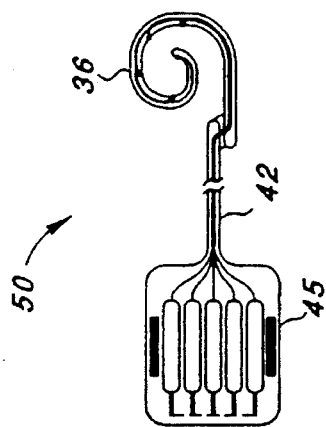

Referring next to FIG. 3, an illustration is shown that depicts the relative size of the multichannel stimulator 50 compared to a representative human ear. FIG. 3 further illustrates where within the human ear the stimulator 50 is implanted. The electrode array 36 is implanted in the cochlea 52 of the ear so as to allow the electrode contacts 38 of the array to make contact with the auditory nerve 54. The flexible body 42 is implanted to snake through the ear channel and up behind the ear to a pocket under the skin whereat the microstimulator array 45 is implanted. An external transmitter coil 56 is then mounted externally so as to be inductively coupled with the coils 30 of the microstimulators 20. The coil 56 is electrically connected to a sound processor 60 by way of a cable 58. Advantageously, the sound processor 60 may be located or carried in any suitable location on the patient, behind the ear, in a shirt pocket, etc.

Figure 4A:
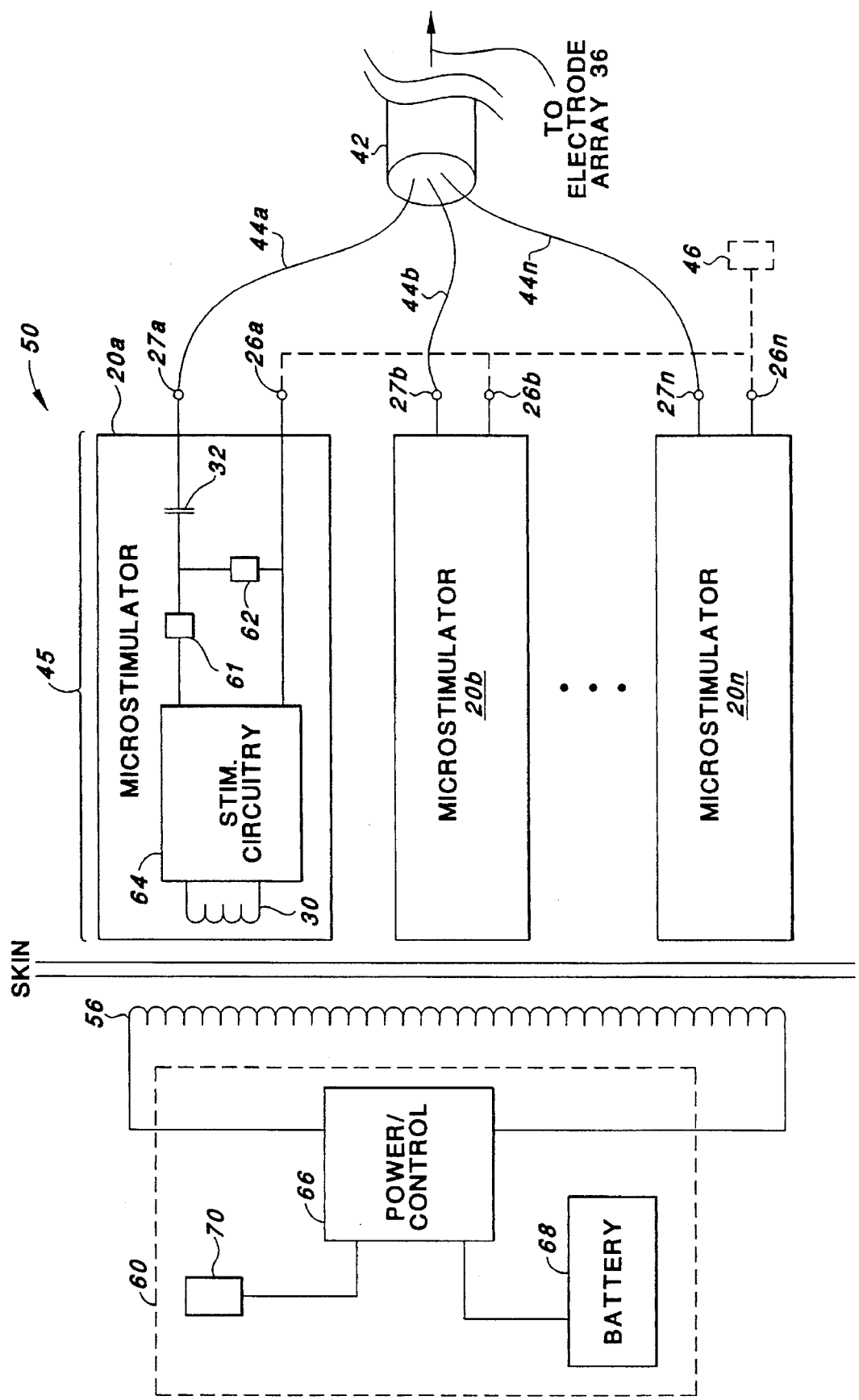
FIG. 4A is a functional block diagram of a multichannel stimulator made in accordance with the present invention, illustrating both the implantable and non-implantable portions thereof.

Turning next to FIG. 4A, a functional block diagram of the multichannel stimulator 50 and the external sound processor 60 are shown. It is noted that the external processor 60 is a sound processor when the invention is used as a multichannel cochlear stimulator. If a different application is involved, then the external processor 60 may be a different kind of processor, as needed for the given application. The multichannel stimulator 50 includes a plurality of microstimulators 20*a*, 20*b*, . . . 20*n* connected in a microstimulator array 45. For the configuration shown in FIG. 4A, one electrode 27*a*, 27*b*, . . . 27*n* of each microstimulator is electrically connected through respective wire conductors 44*a*, 44*b*, . . . 44*n*, of the flexible body 42 to the electrode array 36. The other electrodes 26*a*, 26*b*, . . . 26*n* of each microstimulator are either electrically tied together to form a common indifferent electrode 46, or are electrically isolated from each other to form a plurality of indifferent electrodes.

In the embodiment shown in FIG. 4A, each microstimulator 20 includes a coil 30, stimulation circuitry 64 (located on IC chip 27), first and second current limiters 61 and 62, and a capacitor 32. The current limiters 61 and 62 have their current limiting value controlled by stimulation circuitry 64. When current limiter 61 is set to a non-zero value, the capacitor 32 is charged from power derived from the incoming power signal (inductively coupled from the external coil 56). When current limiter 62 is set to a non-zero value, the capacitor 32 discharges through the electrodes 27 and 26. The current limiters 61 and 62, each of which may be simply a resistor, FET, or equivalent adjustable impedance device (and which is also controlled by the stimulation circuitry 64), thus limit how much current flows between the electrodes 26 and 27 when the capacitor is charging and discharging, respectively. The value of the currents thereby permitted to flow and the periods of time during which they are permitted to flow is advantageously specified by portions of the information transmitted from the external processor 60.

The external processor 60 includes a power/control circuit 66 that drives the external coil 56 with an appropriate modulated power signal, e.g., a carrier signal of between 100–5000 KHz. The power signal is modulated with an address word or code, using an appropriate modulation scheme, such as amplitude modulation (AM), phase-shift keyed (PSK) modulation, frequency modulation (FM), or the like. The stimulation circuitry 64, as explained below, contains demodulation circuitry that strips the address code from the modulated carrier signal and determines if such word or code matches a preassigned code for that particular microstimulator. If so, then the microstimulator discharges its stored charge through its electrodes 26 and 27 as controlled by additional information, e.g., the presence of a trigger command, conveyed by the modulated carrier signal. If not, then no discharge occurs. Hence, by modulating the power signal with an appropriate address word or code, a particular microstimulator within the array of microstimulators may be triggered at a selected time. Each microstimulator, when triggered, produces a stimulation pulse through its own set of electrodes, or channel. Hence, a multichannel stimulator function is provided by simply generating the power signal, inductively coupling it to the internal coils of each microstimulator, and modulating it with desired address codes as a function of which channel is to be stimulated.

The power/control circuit 66 may be of conventional design. Typically, such circuit includes an oscillator to generate the carrier signal, and a suitable modulation circuit to modulate the carrier signal, and appropriate impedance matching circuits to efficiently drive the inductive coil 56. A power source 68, such as a rechargeable battery, is also included within the processor 60 so as to render the processor 60 portable.

Typically, an input transducer 70 is also coupled to the power/control circuit 66. The transducer 70 generates an appropriate input signal used to define or otherwise control the modulation that is applied to the power signal.

Figure 6:
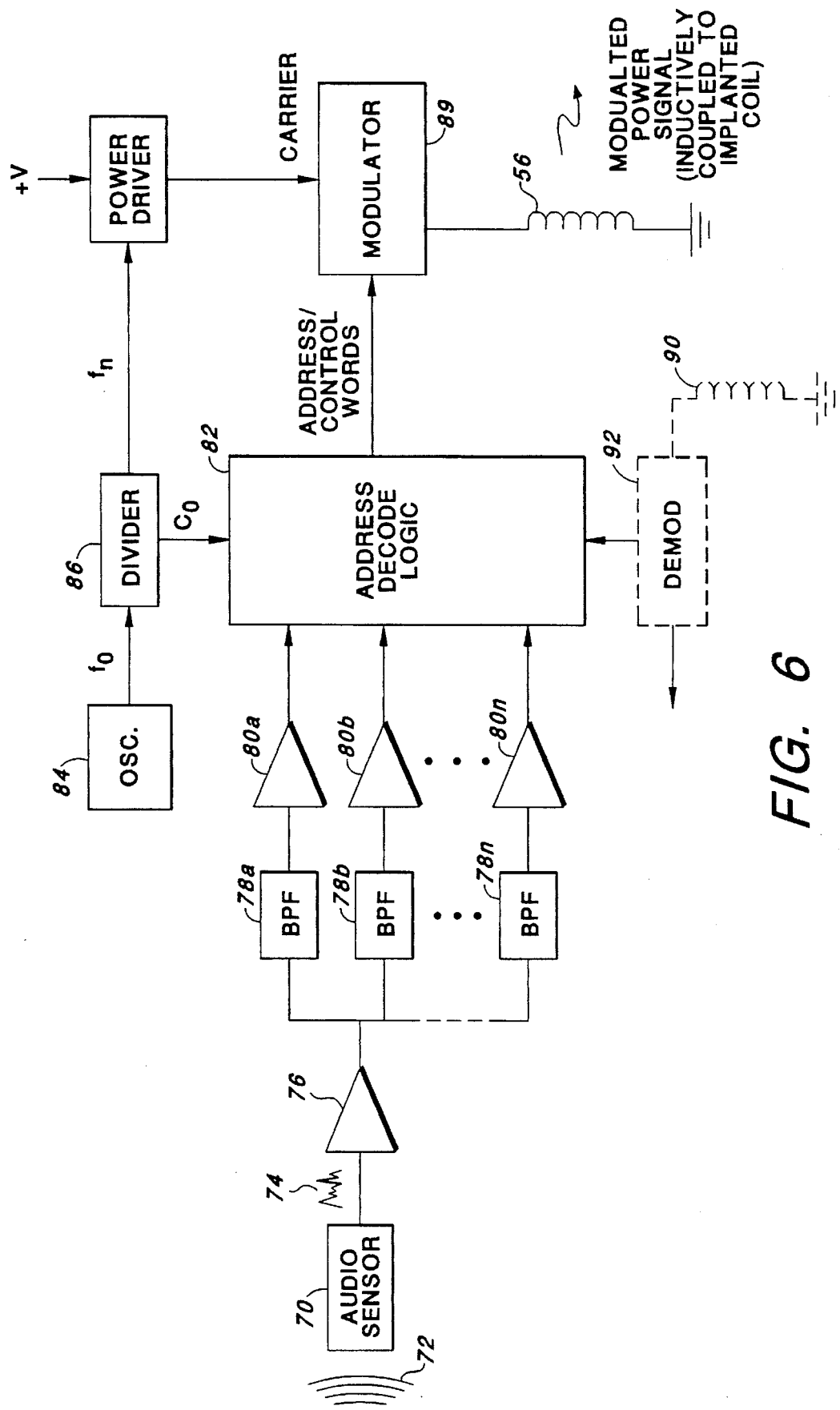
FIG. 6 is a functional block diagram of the external (non-implanted) power/control module of the multichannel stimulator of FIG. 4.

For example, where the processor 60 is a sound processor, and the electrode array 36 is a cochlear array, and where the multichannel stimulator 50 is thus used as a cochlear prosthesis, the transducer 70 may be a microphone that picks up or senses audio signals. A functional block diagram of a processor 60 suitable for such cochlear prosthesis application is illustrated in FIG. 6. As seen in FIG. 6, the microphone 70, or equivalent audio sensor, produces an audio signal 74 in response to audio vibrations 72 picked up by the sensor or transducer 70. The audio signals are amplified in an amplifier 76 and then separated, using appropriate bandpass filter (BPF) circuits 78$a$, 78$b$, . . . 78$n$, into a band of frequencies. The signal components present in each band are then applied to address decode logic 82 through appropriate driver circuits 80$a$, 80$b$, . . . 80$n$. The driver circuits may be as simple as a threshold circuit that assumes a high or low output, with an appropriate time constraint depending upon the amplitude of the signal present at its input.

An oscillator 84 generates a primary signal having a stable frequency, $f_0$, which may be, e.g., within the range of 100 KHz to 50 MHz. A higher frequency is desirable because it can be produced using a smaller-sized crystal within the oscillator circuit. The primary signal is divided by a divider circuit 86 so as to produce a desired carrier signal having frequency, $f_n$, in the range of 100 KHz to 50 MHz. In certain instances, a carrier frequency $f_n$ of 1 to 5 MHz is desirable to provide inductive coupling through a simple inductor coil in which the stray capacitance of the inductive coil provides resonance at the carrier frequency, thereby improving the efficiency of the inductive coupling process. The carrier signal $f_n$, which is typically a low power signal, is converted to an appropriate power signal by a power driver circuit 88. A suitable clock signal, $C_0$, is also derived from the primary signal. The clock signal is used, inter alia, to clock the operation of the address decode logic 82.

The address decode logic 82 generates appropriate address words as a function of the inputs received from the driver circuits 80$a$, 80$b$, . . . 80$n$. The address words are then used to modulate the power signal. The modulated power signal is then applied to the external coil 56. The power associated with the modulated power signal is then inductively coupled into the coils 30 of each microstimulator. The address words are recovered through demodulation, and are thereafter used to trigger appropriate ones of the microstimulators.

In operation, it is seen that the address words that modulate the power signal are generated as a function of the frequency components or content of the audio sounds 72 picked up by the microphone or other transducer 70. That is, the presence of a high frequency component within the input audio signal 72 causes a first address code to be generated that thereafter modulates the power signal. When coupled through the skin to the microstimulators, such modulated power signal causes a particular one of the microstimulators (preferably the one having its channel, or electrodes, more closely coupled to the base of the cochlea, where the higher frequency audio signals normally stimulate the auditory nerve) to be triggered. Similarly, the presence of a middle frequency component within the input audio signal causes a second address code to be generated that thereafter modulates the power signal. When coupled through the skin to the microstimulators, such modulated power signal causes another one of the microstimulators (preferably one having its channel, or electrodes, more closely coupled to the middle cochlea, where the middle frequency audio signals normally stimulate the auditory nerve) to be triggered. Likewise, the presence of a lower frequency component within the input audio signal causes a third address code to be generated that thereafter modulates the power signal. When coupled through the skin to the microstimulators, such modulated power signal causes yet another one of the microstimulators (preferably one having its channel, or electrodes, more closely coupled to the apical cochlea, where the lower frequency audio signals normally stimulate the auditory nerve) to be triggered. In this manner, then, the cochlea is stimulated through multiple channels, as a function of the frequency components of a sensed audio signal, thereby providing an implantable, multichannel cochlear prosthesis.

As further shown in FIG. 6, some embodiments of the invention may further include a receiving coil 90 coupled to a demodulation circuit 92. Such coil 90 is meant to be inductively- or rf-coupled with an implanted microtelemeter device, used as part of the implantable multichannel stimulator. Such microtelemeter device, when used, provides back-telemetry from the implantable multichannel device, as explained more fully below in conjunction with FIG. 9, thereby providing some measure of feedback and/or monitoring capability during operation of the multichannel stimulator system.

Turning back to FIG. 4B, a block diagram of the present invention is shown, as in FIG. 4A, further showing the use of a focusing coil 49 and individual coupling coils 51. The focusing coil 49 captures the magnetic flux generated by the source coil 56 external to the skin, and redirects it in an optimum orientation for being captured by the coils 30 within each microstimulator 20. The focusing coil 49 is a relatively large coil, preferably wound around the periphery of the array 45, and is designed to capture a maximum amount of magnetic flux from the source coil 56. The capturing of such flux causes an equivalent electrical signal to be generated, which electrical signal is applied to each of the individual coupling coils 51a, 51b, ... 51n, shown in FIG. 4B as being connected in series. The application of such electrical signals to the individual coupling coils 51a, 51b, ... 51n, causes additional magnetic flux to be generated that is optimally coupled with the coil 30 of each microstimulator. Thus, in effect, the focusing coil 49 and the individual coupling coils 51 function electrically as an intermediate transformer that couples the external coil 56 to the respective microstimulator coils 30. The use of such arrangement significantly improves the coupling efficiency between the external coil 56 and the microstimulator coils 30, thereby reducing the power needed within the external coil 56 for proper operation of the stimulator 50.

Figure 4B:
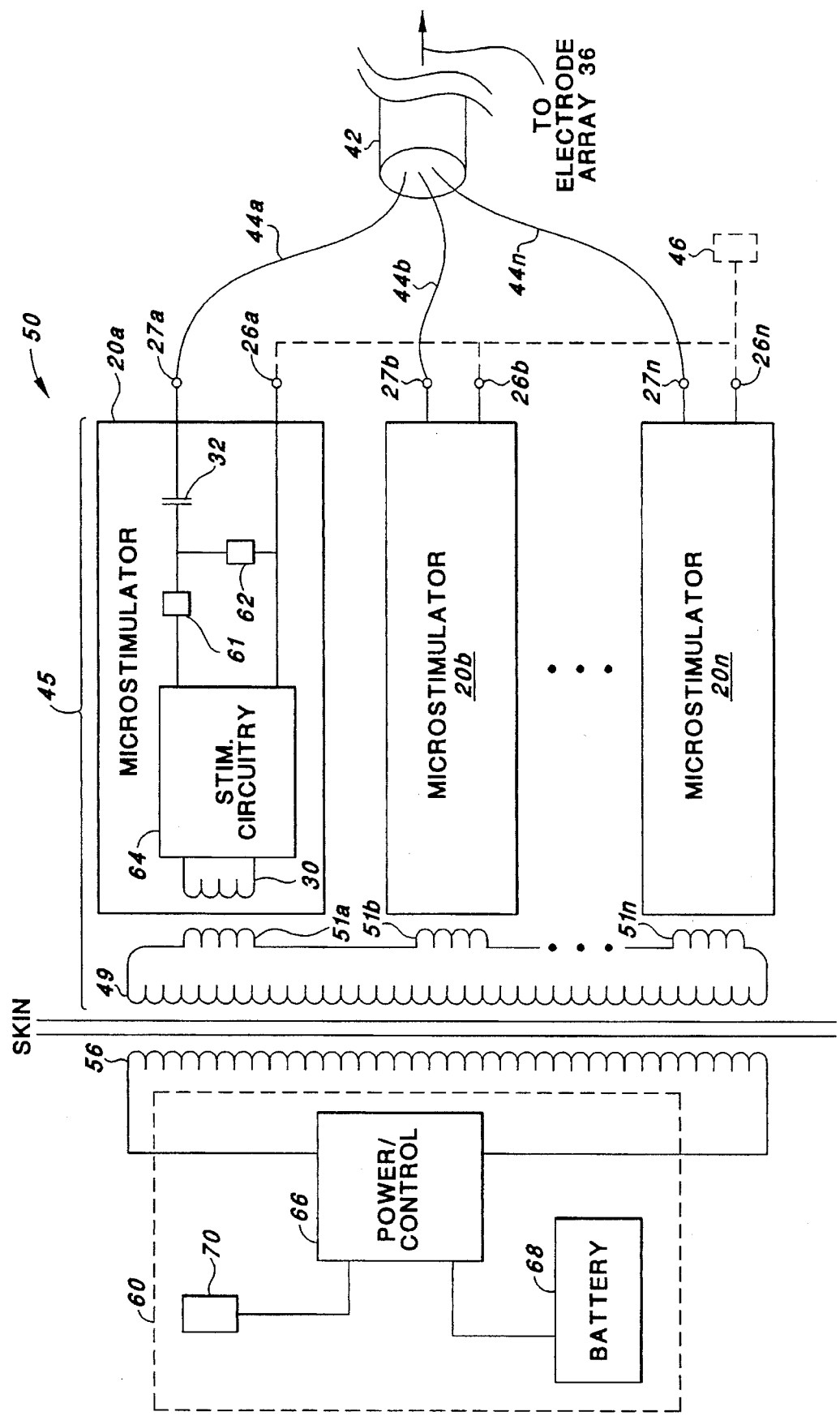
FIG. 4B is a functional block diagram of an alternative embodiment of a multichannel stimulator of the invention wherein power is coupled to each microstimulator through a focusing coil, thereby improving the coupling efficiency.
Figure 4C:
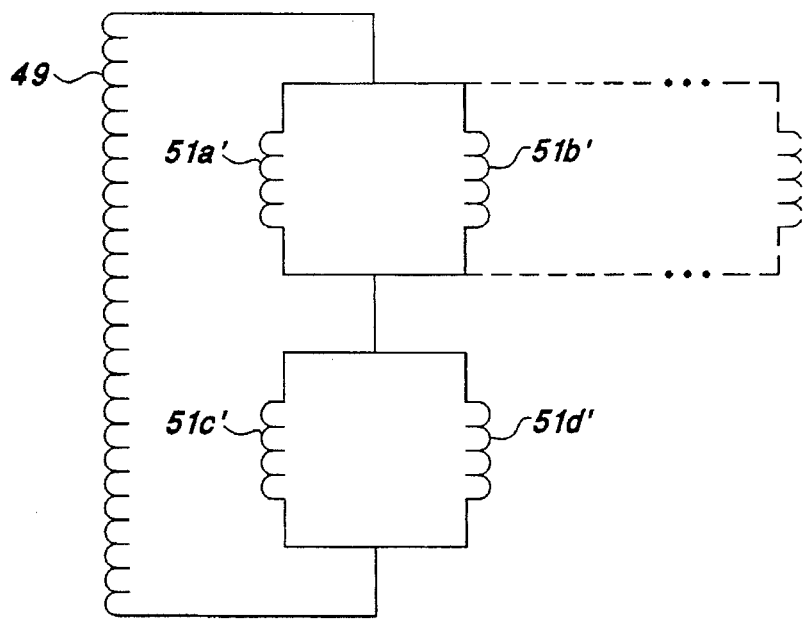
FIGS. 4C and 4D are electrical schematic diagrams that depict variations that may be used to connect secondary coupling coils to the primary focusing coil, in addition to the series arrangement shown in FIG. 4B, in order to improve the coupling efficiency to the microstimulators.

FIG. 4B depicts the individual coupling coils 51, wound around each microstimulator 20, as being connected in series. Such configuration, however, is only exemplary of various connection schemes that may be used. For example, as shown in FIG. 4C, a first pair of coupling coils 51a' and 51b', each being wound around a respective microstimulator, may be connected in parallel, with such parallel configuration being connected in series with a second pair of coupling coils 51c' and 51d'. Additional parallel pairs of coupling coils may be included in such series combination, as required, depending upon the number of microstimulators that are used within the array 45. Further, more than two coils may be included in each parallel combination, as required, again depending upon the number of microstimulators that are used within the array 45. The series combination of parallel pairs is then connected across the focusing coil 49.

Figure 4D:
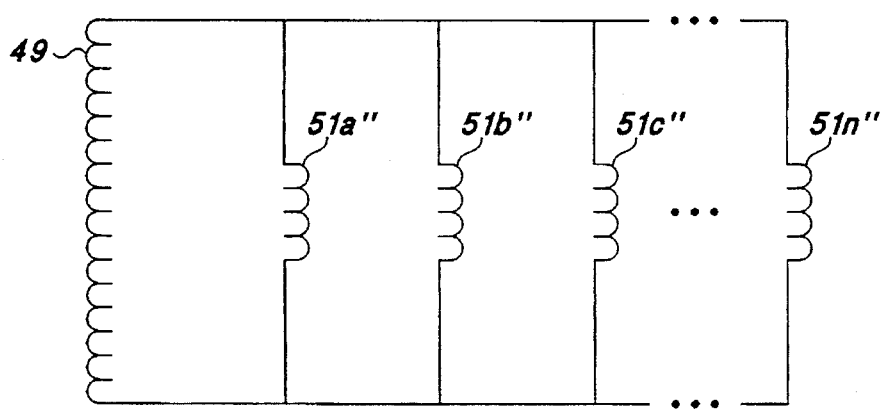

Alternatively, all of the coupling coils 51a", 51b", ... 51n", associated with a given microstimulator array 45 may be connected in parallel as shown in FIG. 4D, with such parallel array being connected across the focusing coil 49.

The particular configuration that should be used—series (FIG. 4B), parallel (FIG. 4D), or a combination of series and parallel (FIG. 4c)—will depend upon which configuration provides the best impedance match between the source coil 56 and the individual microstimulator coils 30. Although any of the configurations may be used, the one that provides the best impedance match provides optimal power transfer through the coils, and is thus the one that is preferred. For most applications, such configuration is of a form as shown in FIG. 4C, with at least two parallel configurations of individual coupling coils being connected in series.

Figure 7A:
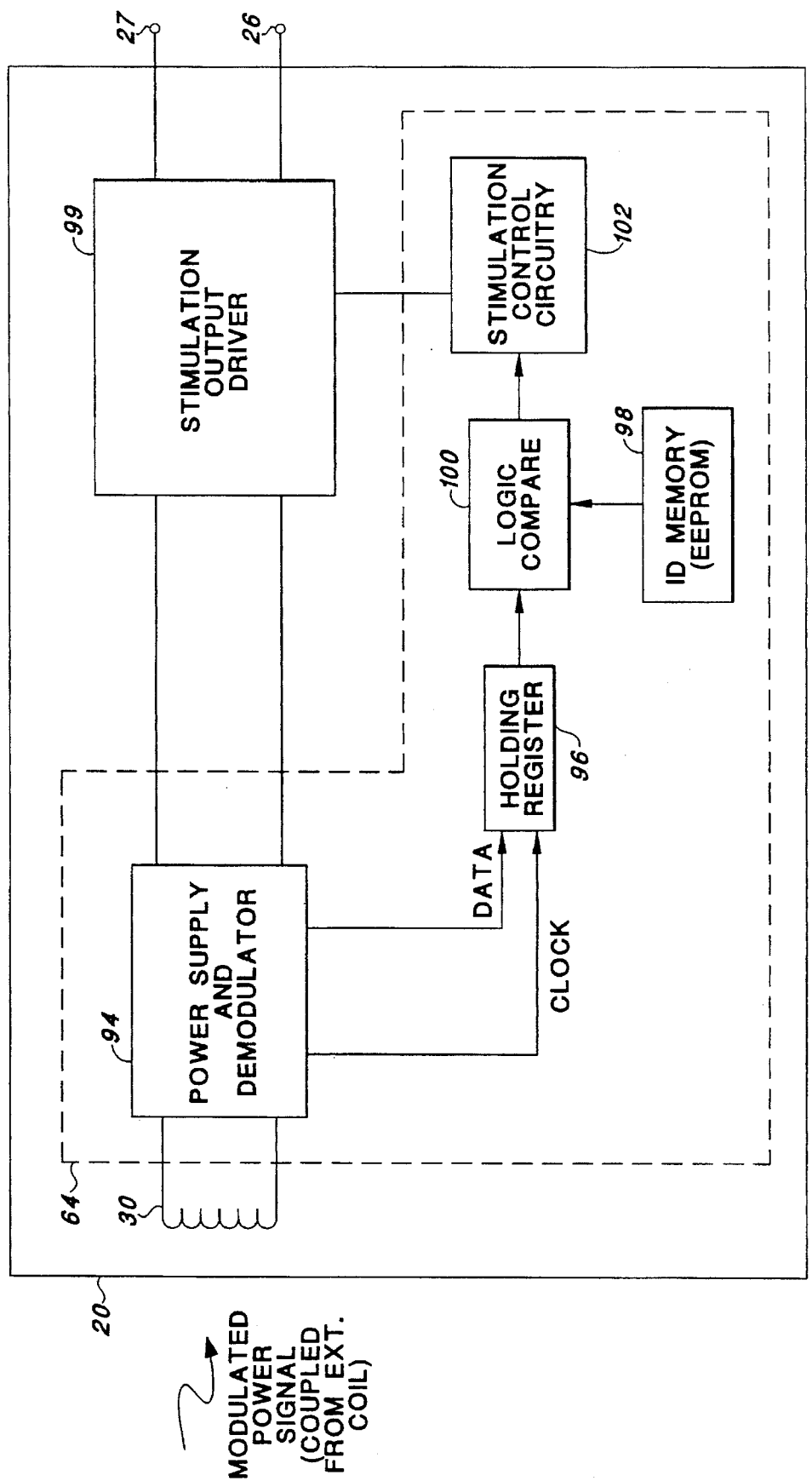
FIG. 7A is a functional block diagram of a microstimulator that may be used within the implantable portion of the multichannel stimulator of FIG. 4.
Figure 7B:
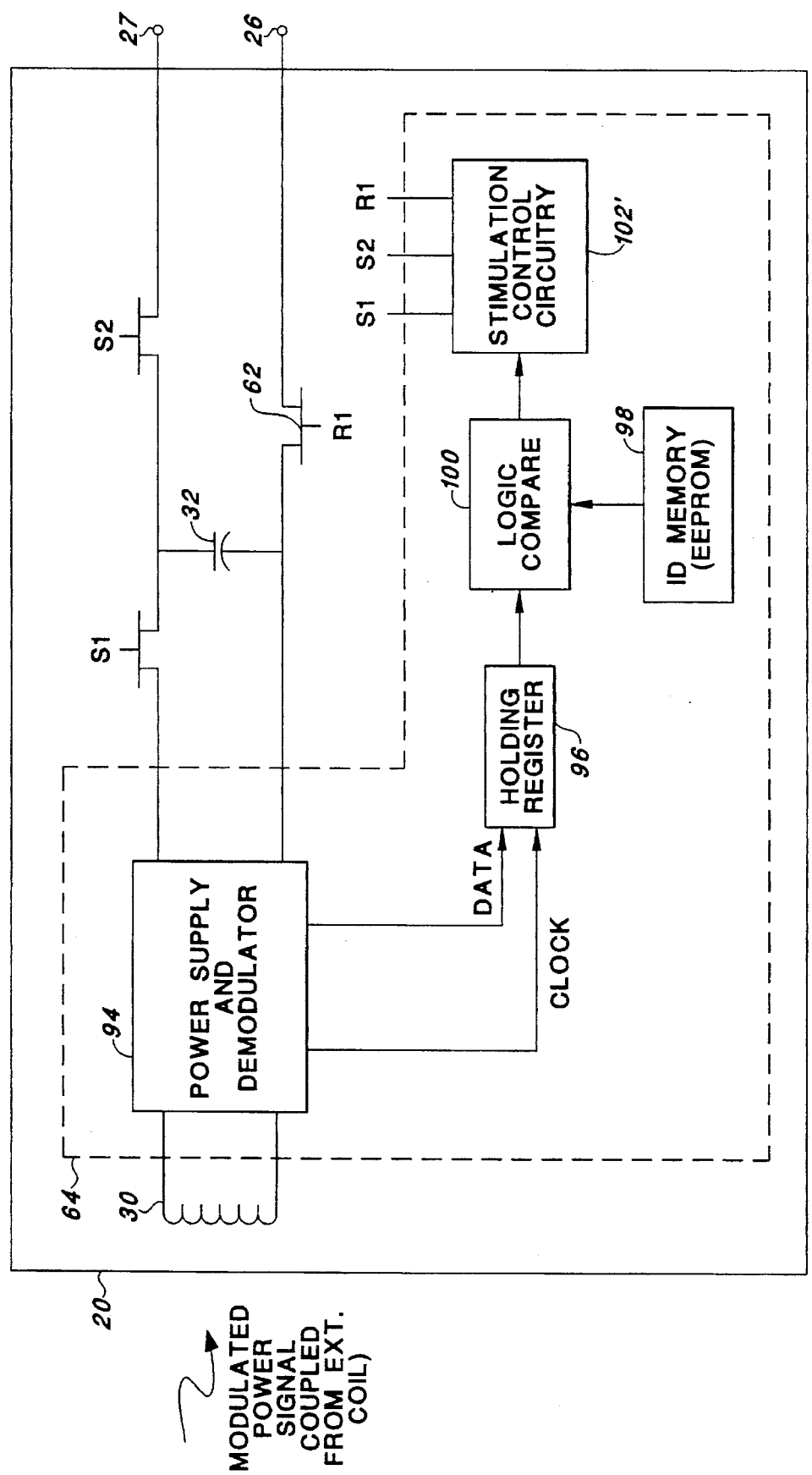
FIG. 7B is a block diagram as in FIG. 7A, showing one embodiment of a stimulation output driver that may be used within a microstimulator used within the implantable portion of the multichannel stimulator of FIG. 4.

Referring next to FIGS. 7A and 7B, a more detailed block diagram of one of the microstimulators 20 used within the implantable multichannel stimulator 50 is shown. Such block diagram functionally illustrates the manner in which the microstimulator 20 is triggered. As seen in FIGS. 7A and 7B, the microstimulator 20 includes a power supply and demodulator circuit 94 connected to the coil 30. The power supply and demodulator circuit 94 produces a power signal, a data signal, and a clock signal. In FIG. 7A, the power signal is applied to a stimulation output driver 99 and is coupled to the output electrodes 27 and 26 as controlled by stimulation control circuitry 102. The data and clock signals are connected to a holding register 96. The data signal is clocked into the holding register 96 and is synchronized appropriately so that the address word, used to modulate the incoming power signal, is recovered and held in the register 96. The contents of the register 96 are compared with an address code previously stored in a memory circuit 98 by a logic compare circuit 100. The memory circuit 98 may be considered as a microstimulator identity (ID) memory because the address code is assigned so as to uniquely identity the particular microstimulator within which it is stored. To this end, the memory circuit 98 is preferably an EEPROM circuit that can be readily programmed during manufacture with a unique address code. Other codes may also be stored in the memory 98, e.g., codes that identify particular states or modes of operation that the microstimulator 20 is to assume as a function of the address word received in the holding register 96, thereby providing some measure of programmability of the microstimulator. The logic compare circuit 100 is coupled to a stimulation control circuit 102. The stimulation control circuit 102 is a simple state machine, e.g., a flip flop, that defines when a proper address, i.e., the address of the microstimulator, has been received. In response to being addressed, the stimulation control circuitry 102 controls the stimulation output driver 99, which may be of the form shown in FIGS. 4A and 4B, so that the stimulation pulse may be applied to the output electrodes 27 and 28.

It is noted that the embodiment of the microstimulator shown in FIG. 7A need not utilize a storage capacitor for formation of the stimulation pulse. That is, for some embodiments of the invention, it is contemplated that the power contained within the stimulation pulse, after demodulation of the power signal identifies a proper address, is used to directly generate the stimulation pulse without storing such power in a storage capacitor. Such type of stimulation may be particularly suited to applications where stimulation pulses are needed at a relatively fast rate, e.g., 800 to 1200 pulses second, and there is not sufficient time to charge a storage capacitor. Back telemetry, as described below, may then be used, as required, to adjust the energy content of the stimulation pulses by controlling the power level of the incident signal applied to the external coil 56, or other transducer (in the event inductive coupling is not used).

In the embodiment shown in FIG. 7B, the power signal charges a capacitor 32 through a FET switch S1. The capacitor 32 is coupled to the output electrodes 27 and 26 through FET switch S2 and linear FET R1. The data and clock signals are connected to a holding register 96, as described above in FIG. 7A. The data signal is clocked into the holding register 96 and is synchronized appropriately so that the address word, used to modulate the incoming power signal, is recovered and held in the register 96. The contents of the register 96 are then compared with an address code previously stored in a memory circuit 98 by a logic compare circuit 100. As indicated above, the memory circuit 98 is preferably an EEPROM circuit that can be readily programmed during manufacture with a unique address code. Other codes may also be stored in the memory 98, e.g., codes that identify particular states or modes of operation that the microstimulator 20 is to assume as a function of the address word received in the holding register 96, thereby providing some measure of programmability of the microstimulator.

Still referring to FIG. 7B, the logic compare circuit 100 is coupled to a stimulation control circuit 102'. The stimulation control circuit 102' comprises a simple state machine that defines three of four states for the microstimulator 20. One state, which is the default state, is a charging state, where switch S1 is closed, and switch S2 is open. During the charging state, power recovered from the incoming power signal is used to charge the capacitor 32. Another state, which is triggered only when the logic compare circuit 100 determines that there is a match between the address word held in the holding register 96 and the address code stored in the memory 98, is a discharge state wherein switch S1 is open, and switch S2 is closed, thereby discharging the charge held on capacitor 32 through the electrodes 27 and 26. The amount of current that flows as a result of such discharge is controlled in large measure by setting the impedance of FET R1 to a desired value. A third state, which may be initiated, e.g., by a power-on condition, or by receipt of a first predefined address word in the holding register 96 (which first predefined address word functions as a first central or command word), sets the charge on the capacitor to a desired initial value, e.g., 0 volts. A fourth state, which may be initiated by receipt of a second predefined address word (or second command word) in the holding register 100, sets the impedance value of the FET R1 to an appropriate value. Such impedance value is selected so as to limit the amount of current that flows during discharge through the discharge path to an appropriate value.

Figure 8:
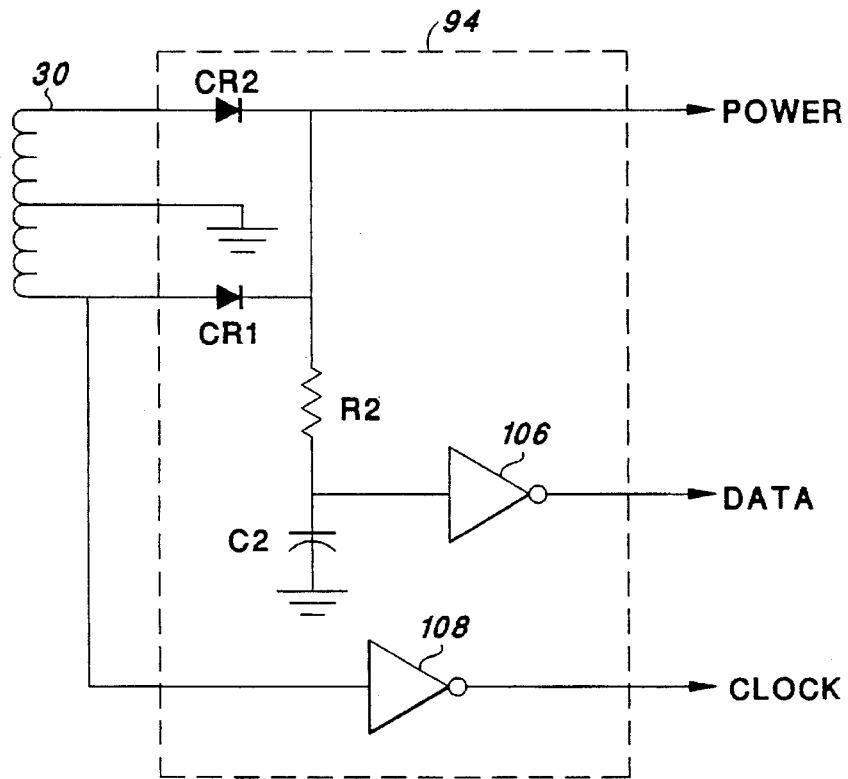
FIG. 8 is a simplified schematic diagram of the power supply/demodulator portion of a microstimulator, where the power signal is modulated using amplitude modulation.

FIG. 8 shows a simplified schematic diagram of a power supply/demodulator circuit that may be used as the power supply/demodulator circuit 94 in FIG. 7, for those situations where the power signal is modulated using amplitude modulation. For this embodiment, the coil 30 is center tapped, with the center tap being connected to ground. The power supply portion of the circuit 94 includes a full-wave rectifier circuit made up of diodes CR1 and CR2. (A bridge rectifier circuit could also be used in the event the coil 30 is not center tapped.) The demodulator portion of the circuit comprises a conventional AM demodulation circuit that includes a filter capacitor C2 and a resistor R2. The time constant defined by the resistor R2 and the capacitor C2 is selected such that the charge on the capacitor C2 follows the AM modulation, but the carrier frequency is filtered out of the signal. A buffer amplifier 106, which may be realized using a conventional inverter circuit, then provides a demodulated data signal. The incoming power signal is also monitored through an additional buffer amplifier 108, which may also be an inverter circuit coupled to one end of the coil 30, so as to provide a clock signal that may be used within the microstimulator, particularly to synchronize and clock the incoming address word data signal.

Figure 9:
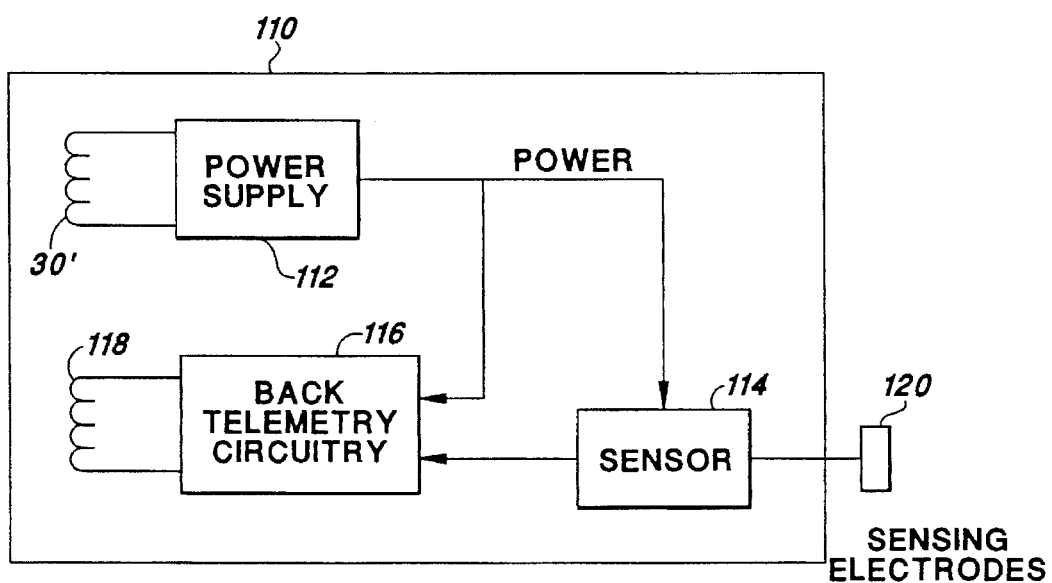
FIG. 9 is a functional block diagram of a microtelemeter device that may be included in some embodiments of the present invention.

Turning next to FIG. 9, a simplified block diagram of a microtelemeter device 110 is shown. In some embodiments of the invention, it is contemplated that such a microtelemeter device, which is housed within a small glass capsule of the type used with the microstimulator 20, may replace one of the microstimulators, or be added to the microstimulators, used within the multichannel microstimulator device 50. Such microtelemeter device serves the function of sensing a designated parameter, or a plurality of parameters, associated with the implanted environment wherein the multichannel stimulator device 50 is placed, and then sending, or telemetering, such sensed parameter(s) back to the external processor 60. Such "back telemetry" function thus provides a measure of feedback or parameter monitoring that allows the processor 60 to better assess and control the operation of the microstimulators.

As seen in FIG. 9, the microtelemeter 110 includes a coil 30' for inductively receiving the power signal. Power derived from such power signal is then used to power a sensor circuit 114 and a back telemetry circuit 116. The sensor circuit 114 may have one or more sensing electrodes 120 connected thereto, which sensors will generally be (but sometimes do not have to be) external to the sealed housing wherein the other microtelemeter circuits are housed. Signals representative of the parameters sensed by the sensor circuit 114 are then used to modulate a back telemetry carrier signal, generated by the back telemetry circuit. The modulated back telemetry carrier signal is then inductively coupled to a receiving coil 90 (FIG. 6) included within the external processor. In some embodiments of the invention, it may be desirable to transmit the back telemetry signal via an appropriate rf link that is established with the external processor 60, rather than coupling such signal inductively with the external coil 90.

The types of parameters that may be sensed by the sensor circuit 114 include body temperature, body movement, an electromyogram, an electroneurogram, respiration rate, heart rate, glucose level, blood pH, blood oxygen, and the like. In addition, internal parameters associated with the operation of the microtelemeter device 110 or the multichannel stimulator 50 may also be sensed, such as charge voltage, current state of the control circuits, and the like.

In some embodiments of the invention, each or selected ones of the microstimulators 20 are modified to include a back telemetry function, so that each such microstimulator is, in effect, a microstimulator/microtelemeter device. Such dual function microdevice requires a somewhat larger housing, and may not be needed nor desired for many applications.

Figure 10:
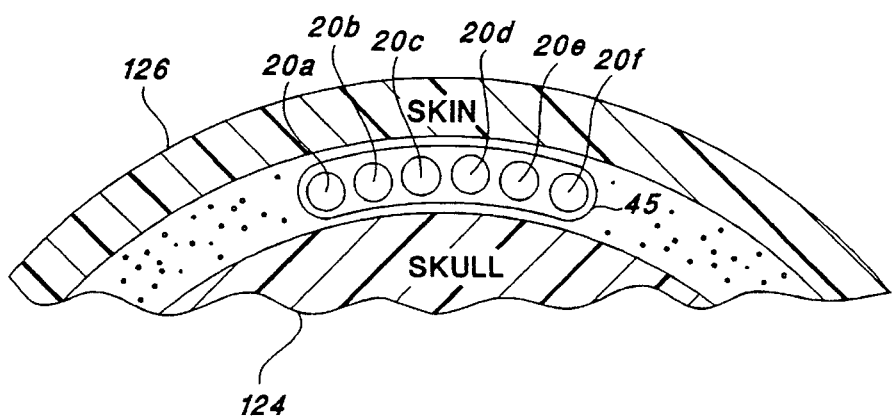
FIG. 10 illustrates how the flexibility of a multichannel microstimulator made in accordance with the invention facilitates its implantation and form fit near the curved skull of a patient.

Turning next to FIG. 10, a cross-sectional view of an implanted multichannel stimulator 45 made in accordance with the invention is shown. As seen in FIG. 10, such stimulator 45 is placed next to the skull 124 of a patient, under the skin 126. Where the material within which the individual microstimulators 20a, 20b, . . . are implanted is a flexible elastomer, e.g., silicone rubber, then the stimulator 45 is flexible and can readily be formed to snugly fit against the curved skull 124. Such flexibility is made possible due to the individual microstimulators that make up the device, all of which are sealed within the stimulator 45 to form an integral unit.

Those of skill in the art will readily recognize that the above descriptions of the circuitry within the microstimulator 20, multichannel stimulator 50, and/or microtelemeter 110, are somewhat simplified. For example, when clocking data into the holding register 96, it may be desirable to use stop bits and parity bits, and appropriate logic circuitry to detect such bits, to help assure the proper framing of a given data word. However, any such additional circuitry that is used may be of conventional design, and it is submitted that sufficient information is presented herein to enable a person of skill in the art to readily practice the invention.

As described above, it is seen that the present invention provides an implantable multichannel stimulator that is easy and inexpensive to manufacture. The manufacturing costs are kept low because the multichannel stimulator utilizes an implanted portion and a non-implanted portion, with the main part of the implanted portion being very small, e.g., less than about 20 mm by 15 mm by 3 mm, and because such main part is made from a plurality of substantially identical sealed microstimulator devices, each of which operates independently of the others. Thus, if one should fail, the others will keep working. Further, the use of complex, power-consuming, implanted multiplexing circuitry is avoided.

As further described above, it is seen that the present invention avoids the use of through-the-skin connectors to couple control signals or power signals to the implanted portions of the stimulator.

Moreover, as seen from the above description, the present invention provides, in one application thereof, a multichannel stimulator that, when coupled to an intracochlear electrode array, provides a cochlear prothesis that enables the profoundly deaf to experience the sensation of hearing without requiring the use of through-the-skin electrical connectors to electrically contact the electrode array.

While the invention herein disclosed has been described by means of specific embodiments and applications thereof, numerous modifications and variations could be made thereto by those skilled in the art without departing from the scope of the invention set forth in the claims.

What is claimed is:

1. A multichannel stimulation system comprising:

a plurality of implanted electrodes;

a plurality of implantable microstimulators, each being electrically connected to at least two of said plurality of implanted electrodes, each microstimulator including:

first coupling means for receiving a power signal and an informational signal;

stimulation circuitry powered by said power signal including:

power means for extracting power from said power signal, demodulator means for recovering and demodulating said information signal, output circuitry responsive to said information signal for applying a stimulation pulse, derived from the power extracted from said power signal, to said implanted electrodes whenever said information signal contains prescribed stimulator codes, whereby the stimulation pulse may be selectively applied to the electrodes connected to a respective one of said plurality of microstimulators as controlled by said information signal;

a biocompatible, non-conductive plastic material adapted for binding said plurality of microstimulators together to form a stimulator array; and an external control unit that includes:

first generating means for generating said power signal, second generating means for selectively generating said information signal, and second coupling means for transmitting said power and information signals.

2. The multichannel stimulation system as set forth in claim 1 wherein said external control unit includes modulation means for modulating said power signal with said information signal and wherein said demodulator means of each of said microstimulators includes means for demodulating said power signal to recover said information signal therefrom.

3. The multichannel stimulation system as set forth in claim 1 further including an electrode array comprising said plurality of electrodes spaced apart in a prescribed relationship, each of said plurality of electrodes being connected to at least one of said plurality of implantable microstimulators.

4. The multichannel stimulation system as set forth in claim 3 wherein said plastic material is further adapted for binding said electrode array to said stimulator array.

5. The multichannel stimulation system as set forth in claim 3 wherein said stimulator array includes at least four microstimulators.

6. The multichannel stimulation system as set forth in claim 5 wherein said plastic material that binds together said plurality of microstimulators to form said stimulator array comprises silicone rubber.

7. The multichannel stimulation system as set forth in claim 4 wherein said plastic material that binds together said plurality of microstimulators to form said stimulator array has a sufficient flexibility to allow said stimulator array to bend and flex, thereby allowing said stimulator array to be form fit against a curved surface.

8. The multichannel stimulation system as set forth in claim 4 wherein said first and second coupling means comprise first and second coils, respectively, and wherein said first and second coils are inductively coupled to each other.

9. The multichannel stimulation system as set forth in claim 8 further including:

a formed length of said plastic material which binds said stimulator array, said formed length extending out from and being an integral part of said stimulator array, said formed length further having a distal end; and a plurality of conductive wires connecting said electrode array to said stimulator array, said conductive wires being sealed within said formed length of said plastic material, said electrode array including said plurality of electrode contacts that are connected to said plurality of conductive wires proximate said distal end of said formed length.

10. The multichannel stimulation system as set forth in claim 9 wherein said formed length is dimensioned for insertion in the cochlea of a human ear, with said electrode contacts being positioned so as to stimulate an auditory nerve, and with said stimulator array being implanted adjacent to the ear so that the first coil means within each of said microstimulators is oriented to be inductively coupled to the second coil means of the external control unit when said second coil means is positioned so as to be proximate said ear.

11. The multichannel stimulation system as set forth in claim 8 further including an intermediate coil having a focusing coil and a plurality of respective individual coils, said focusing coil being formed within the plastic material of said stimulator array such that the turns of such focusing coil are located near a periphery of such stimulator array, each of said individual coils being wound around a respective one of said microstimulators, and each of said individual coils being connected in circuit relationship with said focusing coil, said first coil being inductively coupled with said focusing coil, and said individual coils being inductively coupled with a respective one of said second coils, whereby said first and second coils are inductively coupled to each other through said intermediate coil.

12. The multichannel stimulation system as set forth in claim 11 wherein said individual coils are connected in series with said focusing coil.

13. The multichannel stimulation system as set forth in claim 11 wherein said individual coils are connected in parallel with said focusing coil.

14. The multichannel stimulation system as set forth in claim 11 wherein a first group of said individual coils are connected in parallel with each other, and a second group of said individual coils are connected in parallel with each other, and wherein said first and second groups of individual coils are connected in series with said focusing coil.

15. The multichannel stimulation system as set forth in claim 4 wherein each of said microstimulators includes a capacitor coupled to the respective electrodes of the microstimulator, and wherein said power means includes means for charging said capacitor with an electrical charge derived from said power signal.

16. The multichannel stimulation system as set forth in claim 15 wherein said demodulator means includes:

memory means for storing prescribed stimulator codes, comparison means for comparing the recovered information signal with said prescribed stimulator codes and for generating a trigger signal when said recovered information signal bears a prescribed relationship with said prescribed stimulator codes, and current regulator means controlled by said trigger signal for discharging said capacitor, whereby the electrical charge on said capacitor may be selectively applied to the respective electrode as controlled by said information signal.

17. The multichannel stimulation system as set forth in claim 1 wherein said external control unit includes a means for receiving a back telemetry signal and each of said microstimulators includes means for sensing a prescribed parameter and means for telemetering said back telemetry signal to said external control unit, said back telemetry signal being derived from said sensed prescribed parameter, whereby said external control unit is provided with information concerning said sensed prescribed parameter.

18. The multichannel stimulation system as set forth in claim 1 wherein each of said microstimulators includes means for sensing a prescribed parameter and said multichannel stimulation system further includes a microtelemeter that is bound to said plurality of microstimulators as part of said stimulator array, said microtelemeter including means for generating a back telemetry signal as a function of said sensed parameters and telemetering said back telemetry signal to said external control unit.

19. An implantable multichannel stimulator comprising:

an electrode array including;

a plurality of electrode contacts, a plurality of wire connectors, each of said wire connectors electrically connected to one of said electrode contacts, insulating material disposed within said electrode array such that each of said wire conductors associated with each electrode contact is electrically insulated from the other wire conductors associated with the other electrode contacts; and a plurality of implantable microstimulators, each of which includes;

a first and second output terminal connected to prescribed selected ones of said wire conductors of said electrode array, means for applying a stimulation pulse between said first and second output terminals in a controlled manner, and a bonding material disposed proximate to said plurality of implantable microstimulators such that said plurality of implantable microstimulators are mechanically held together, said bonding material being compatible with and impervious to body fluids;

whereby selected ones of said electrode contacts of said electrode array have said stimulation pulse applied thereto in response to a controlled application of stimulation pluses from at least one of said microstimulators.

20. The implantable multichannel stimulator as set forth in claim 19 wherein each of said plurality of microstimulators further includes:

first coupling means for receiving a power signal and an informational signal;

means for applying a stimulation pulse between said first and second output terminals from power derived from said power signal whenever said informational signal contains a preassigned stimulator code;

whereby a stimulation pulse is selectively applied to the respective electrode as controlled by said informational signal.

21. The implantable multichannel stimulator as set forth in claim 20 wherein said bonding material comprises a plastic material that encapsulates said plurality of microstimulators so as to form a stimulator array, said plastic material imparting a degree of flexibility to said stimulator array that permits said stimulator array to bend and flex so as to allow said stimulator array to be form fit against a curved surface.

22. The implantable multichannel stimulator as set forth in claim 20 wherein said power signal is modulated with said informational signal, and wherein each of said microstimulators includes means for demodulating said power signal to recover said informational signal.

23. The implantable multichannel stimulator as set forth in claim 20 wherein each of said plurality of microstimulators further includes a capacitor coupled to said first and second output terminals, and power supply means for charging said capacitor with an electrical charge derived from said power signal.

24. The implantable multichannel stimulator as set forth in claim 23 wherein each of said microstimulators further includes current regulator means connected to said capacitor for selectively removing any electrical charge on said capacitor.

25. The implantable multichannel stimulator as set forth in claim 24 further including means for generating an initialization signal and wherein said current regulator means is controlled by said initialization signal, said initialization signal being generated whenever said power signal is first received by the microstimulator, whereby any initial charge on said capacitor when power is first applied to said microstimulator is removed, thereby rendering said electrical charge on said capacitor to a known value.

26. The implantable multichannel stimulator as set forth in claim 20 further including a common electrode wherein one of said first or second output terminals from each of said microstimulators is connected to said common electrode, and where the other of said first or second output terminals from each of said microstimulators is connected to one of said electrode contacts of said electrode array, whereby unipolar stimulation occurs between the electrode contacts of said electrode array and said common electrode.

27. The implantable multichannel stimulator as set forth in claim 20 wherein said first and second output terminals from each of said microstimulators are connected to respective ones of said electrode contacts of said electrode array, whereby bipolar stimulation occurs between the electrode contacts of said electrode array connected to the first and second output terminals of each of said microstimulators.

28. The implantable multichannel stimulator as set forth in claim 20 further comprising a common electrode and wherein at least one of said plurality of microstimulators includes means for switching to selectively connect one of said first or second output terminals to said common electrode, whereby unipolar stimulation may be selectively provided.

29. The implantable multichannel stimulator as set forth in claim 28 wherein at least one of the microstimulators is connected to the output terminals of at least another of the microstimulators and includes said switching means to selectively provide a sequence of unipolar stimulation followed by bipolar stimulation.

30. The implanatable multichannel stimulator as set forth in claim 20 wherein the number of microstimulators included within said plurality of microstimulators comprises at least four.

31. The implantable multichannel stimulator as set forth in claim 20 wherein said bonding material is silicon rubber and said at least four microstimulators are bound together by said silicone rubber.

32. The implantable multichannel stimulator as set forth in claim 31 further including:

a formed length of silicon rubber, said formed length extending out from and being an integral part of said silicon rubber bonding material, said formed length further having a distal end;

wherein at least a portion of said wire conductors that connect said electrode contacts of said electrode array to said microstimulators are formed in said length of silicone rubber, said electrode contacts being connected to said plurality of said wire conductors proximate said distal end of said formed length.

33. The implantable multichannel stimulator as set forth in claim 32 wherein said first coupling means comprises a coil included within each one of said microstimulators that is adapted for inductively receiving said power signal.

34. The implantable multichannel stimulator as set forth in claim 33 wherein said formed length is dimensioned for insertion in the cochlea of a human ear, with said electrode contacts being positioned so as to stimulate auditory nerves, and wherein said at least four microstimulators bound by the silicone rubber form an implantable body that may be implanted adjacent the ear so that the coil within each of said microstimulators is oriented to be inductively coupled to the external coil.

35. The implantable multichannel stimulator as set forth in claim 20 wherein said first coupling means comprises a coil included within each one of said microstimulators that is adapted for inductively receiving said power signal.

36. The implantable multichannel stimulator as set forth in claim 35 wherein said coil of each microstimulator is inductively coupled with an external coil through an intermediate coil formed within said electrode array.

37. The implantable multichannel stimulator as set forth in claim 36 wherein said intermediate coil includes a primary winding wrapped around a periphery of said mechanically-held-together microstimulators, and a plurality of secondary windings, each secondary winding wrapped around a periphery of one of said microstimulators.

38. The implantable multichannel stimulator as set forth in claim 37 wherein said secondary windings are connected in series.

39. The implantable multichannel stimulator as set forth in claim 37 wherein said secondary windings are connected in parallel.

40. The implantable multichannel stimulator as set forth in claim 37 wherein a first group of said secondary windings are connected in parallel, and a second group of said secondary windings are connected in parallel, and wherein said first group is connected in series with said second group.

41. The implantable multichannel stimulator as set forth in claim 19 further including;

means for sensing a prescribed parameter, and a microtelemeter that is mechanically held to the plurality of microstimulators by said bonding material, said microtelemeter including means for generating a back telemetry signal as a function of said sensed parameter and telemetering the back telemetry signal to a location remote from said multichannel stimulator.

42. The implantable multichannel stimulator as set forth in claim 19 wherein each of said plurality of implantable microstimulators includes means for sensing a prescribed parameter and means for telemetering a back telemetry signal, said back telemetry signal being derived from the sensed prescribed parameter.

43. A method of stimulating multiple channels of an implantable electrode array, said electrode array including a plurality of electrode contacts, each being connected to a respective, insulated wire conductor, and an implanted coil in a sealed housing for each stimulation channel that is to be provided, said method comprising the steps of:

(a) inductively coupling said implanted coil with an external coil;

(b) applying an ac power signal to said external coil;

(c) rectifying the ac power signal that is inductively coupled to the implanted coil of each channel;

(d) charging a capacitor within the sealed housing of each channel with the rectified power signal; and (e) selectively discharging the capacitor of each channel through which stimulation is to be provided through an electrical path that includes a selected one of said wire conductors and the electrode contact connected to said wire conductor.

44. The method as set forth in claim 43 wherein a unique address code is stored in a memory circuit within the sealed housing of each channel, and the method further includes:

modulating the ac power signal applied to the external coil in step (b) with an address word that identifies a particular channel through which stimulation is to be provided;

demodulating the ac power signal received at the implanted coil to recover the address word therefrom;

comparing the recovered address word with the address code stored in the memory circuit of each channel and discharging the capacitor only if the address word is the same as, or bears a prescribed relationship to, the stored address code;

whereby stimulation is selectively provided through multiple channels as a function of the modulation of the ac power signal that is applied to the external coil.

45. A method of stimulating multiple channels of an implantable electrode array, said electrode array including a plurality of microstimulators mechanically held together, each having electrode contacts, each being connected to a respective, insulated wire conductor, said method comprising the steps of:

(a) coupling power to each microstimulator from an external source;

(b) modulating the coupled power with a microstimulator code corresponding to a particular microstimulator of said plurality of microstimulators where a stimulation pulse is to be generated;

(c) demodulating the coupled power at each microstimulator to determine if it contains a preassigned microstimulator code corresponding to the particular microstimulator whereat the demodulation is made; and (d) generating a stimulation pulse from power derived from said coupled power when the microstimulator code corresponds to the preassigned microstimulator code of the microstimulator whereat the demodulation takes place.

46. The method as set forth in claim 45 further including:

(e) monitoring a prescribed parameter of at least one of said plurality of microstimulators;

(f) generating a back telemetry signal indicative of the monitored prescribed parameter; and (g) telemetering the back telemetry signal back to the external source.

47. The method as set forth in claim 46 wherein step (e) comprises monitoring the power coupled into each microstimulator from the external source.

48. The method as set forth in claim 46 wherein step (e) further includes monitoring said prescribed parameter, and wherein said prescribed parameter is selected from the group of: body temperature, body movement, an electromyogram, an electroneurogram, respiration rate, heart rate, glucose level, blood pH, blood oxygen, charge voltage, and a control state of the microstimulator.

* * * * *